United States Patent [19]

McGarry

[11] 4,374,264
[45] Feb. 15, 1983

[54] PROCESS FOR THE PREPARATION OF γ-UNSATURATED CARBOXYLATES

[75] Inventor: Errol J. McGarry, Eltham North, Australia

[73] Assignee: ICI Australia Limited, Melbourne, Australia

[21] Appl. No.: 265,073

[22] Filed: May 18, 1981

[30] Foreign Application Priority Data

Jun. 2, 1980 [AU] Australia ............................. PE3836

[51] Int. Cl.³ .......................................... C07C 69/533
[52] U.S. Cl. .................................................. 560/205
[58] Field of Search ....................... 560/205, 217, 219

[56] References Cited

U.S. PATENT DOCUMENTS 4,113,968  9/1978  Mori et al. .......................... 560/219

FOREIGN PATENT DOCUMENTS 491852  3/1975  Australia .

OTHER PUBLICATIONS

Kondo, Kiyosi et al., "New Synthesis of the Acid Moiety of Pyrethroids", pp. 128–136 of ACS Symposium Series 42, *Synthetic Pyrethroids*, Elliott, Michael, ed. (1976).
Johnson, William S. et al., *J. Am. Chem. Society*, vol. 92 (1970), pp. 741–743.
CRC Handbook of Chemistry and Physics, 60th ed. (1979–1980) p. C-408.

*Primary Examiner*—Natalie Trousof
*Assistant Examiner*—L. Hendriksen

[57] ABSTRACT

The invention concerns a process for the preparation of γ-unsaturated carboxylic acid methyl esters by reacting an allyl alcohol with an excess of trimethyl orthoacetate in the presence of an acidic catalyst. The process involves: the slow addition of the allyl alcohol to trimethyl orthoacetate heated to a temperature at or near its boiling point; removal of portion of the trimethyl orthoacetate from the reaction mixture by distillation; and heating the remaining reaction mixture at a temperature of 130° to 160° C. to complete the reaction.

9 Claims, No Drawings

PROCESS FOR THE PREPARATION OF γ-UNSATURATED CARBOXYLATES

The invention concerns a process for the preparation of γ-unsaturated carboxylic acid esters.

γ-Unsaturated carboxylates are useful intermediates in the preparation of the acid moiety of insecticidal cyclopropane carboxylates which are known in the art as pyrethroid insecticides.

In 1970 W S Johnson et al, Journal of the American Chemical Society, 92, 741 (1970), published a process for the preparation of γ-unsaturated carboxylates by heating a mixture of an allylic alcohol and a large molar excess (seven equivalents) of triethylorthoacetate in the presence of a weak acid catalyst.

In Australian Pat. No. 491 852 K Kondo et al disclose processes for the preparation of cyclopropanecarboxylate esters in which the Johnson reaction is used to prepare the intermediate γ-unsaturated carboxylates. The specification of this patent teaches that the reaction is preferably carried out in two stages in the presence of an acid catalyst and a 20 to 100% excess of the orthocarboxylate.

A later publication by Y Ohmura et al (Japanese patent application No. 76-30067; Japanese Patent Early Publication No. 77-111513) discloses a process for the preparation of methyl 3,3-dimethylpent-4-enoate by the reaction of a mixture of 3-methylbut-2-enol (prenol) and trimethyl orthoacetate in the presence of an acid catalyst. This specification teaches that methyl 3,3-dimethylpent-4-enoate can be prepared in a yield of 81.3% if prenol is reacted with a 4 fold molar excess of trimethyl orthoacetate in a two stage reaction.

In an effort to find a process suitable for the preparation of methyl 3,3-dimethylpent-4-enoate on a large scale, attempts were made to repeat the process taught in the abovementioned Japanese patent application. However, repeated attempts resulted in yields of methyl 3,3-dimethylpent-4-enoate of the order of 35 to 40% which is unsatisfactory for large scale synthesis.

In view of the poor yields of methyl 3,3-dimethylpent-4-enoate obtained by prior art processes the reaction has been closely studied in an attempt to find a process suitable for the preparation of the compound in good yield. As a result of these investigations it has now been found that good yields of γ-unsaturated carboxylic acid methyl esters can be obtained by the slow addition of an allyl alcohol to heated trimethyl orthoacetate.

Accordingly the invention provides a process for the preparation of a γ-unsaturated carboxylate of the formula I

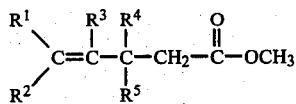

wherein $R^1$, $R^2$, $R^3$, $R^4$ and $R^5$ are independently chosen from hydrogen and $C_1$ to $C_6$ alkyl by the reaction of an allyl alcohol of the formula II

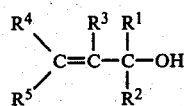

with trimethyl orthoacetate in the presence of an acidic catalyst which process comprises:

(a) slowly adding the allyl alcohol of formula II to a stoichiometric excess of trimethyl orthoacetate heated to a temperature at or near its boiling point;

(b) distilling portion of the excess trimethyl orthoacetate from the reaction mixture until the reaction mixture reaches a temperature in the range from 130° to 160° C.; and (c) maintaining the temperature of the reaction mixture in the range from 130° to 160° C. to complete the reaction.

The prior art processes hereinbefore discussed teach the preparation of γ-unsaturated carboxylates by mixing together an allyl alcohol, an excess of an orthocarboxylate and an acidic catalyst and heating the reaction mixture. In contrast in the process of the present invention an unexpected, significant improvement in the yield of γ-unsaturated carboxylic acid methyl esters has been obtained by the slow addition of an allyl alcohol, in the presence of an acidic catalyst, to an excess of trimethyl orthoacetate heated to a temperature at or near its boiling point.

Surprisingly, it also has been found that the yield of γ-unsaturated carboxylic acid methyl esters is further improved if, after completion of the addition of the allyl alcohol to the hot trimethyl orthoacetate, portion of the excess trimethyl orthoacetate is distilled from the reaction mixture until the temperature of the reaction mixture reaches 130° to 160° C., and then the reaction mixture is heated at a temperature of 130° to 160° C. until the reaction is complete before removing the remaining excess trimethyl orthoacetate from the product.

The process of the invention may be used to particular advantage in the preparation of methyl 3,3-dimethylpent-4-enoate by the reaction of 3-methylbut-2-enol (prenol) with trimethyl orthoacetate.

The nature of the catalyst used in the process of the invention is not narrowly critical. A wide range of acid catalysts may be employed including inorganic acids such as phosphoric acid, hydrochloric acid and sulfuric acid; Lewis acids such as aluminium chloride, zinc chloride and ferric chloride; phenols such as phenol, alkylphenols (eg the cresols and xylenols), nitrophenols and the naphthols; aliphatic and aromatic carboxylic acids such as the $C_1$ to $C_6$ aliphatic carboxylic acids, cyclohexane carboxylic acids and benzoic acids; and aliphatic and aromatic sulfonic acids such as the methane—sulfonic acids and the benzenesulfonic acids. Preferred acidic catalysts include inorganic acids and phenols. More preferred catalysts include orthophosphoric acid and phenol. Particularly preferred catalysts include orthophosphoric acid.

The amount of catalyst used in the process of the present invention is not narrowly critical. Usually the amount of catalyst employed ranges from 1 to 10 mole percent of the allyl alcohol reactant.

In the reaction which is the subject of the process of the present invention 1 mole of an allyl alcohol reacts with one mole of trimethyl orthoacetate to yield 1 mole of the methyl ester of a γ-unsaturated carboxylic acid. However, in practice it has been found that an excess of trimethyl orthoacetate must be employed in order to obtain good yields of the γ-unsaturated carboxylate. For example, in the reaction of prenol with trimethyl orthoacetate it has been found that if the mole ratio of trimethyl orthoacetate to prenol is reduced below 3:1 then the yield of methyl 3,3-dimethylpent-4-enoate is reduced. Therefore, in the process of the present invention it is preferred that the mole ratio of trimethyl orthoacetate to allyl alcohol used is at least 3:1.

In the process of the present invention the trimethyl orthoacetate is first heated to a temperature close to its boiling point and then the allyl alcohol is slowly added. The temperature to which the trimethyl orthoacetate is heated to preferably in the range from 90° to 120° C., and more preferably from 100° to 110° C., and the reaction mixture is maintained at this temperature during the addition.

The period of time over which the allyl alcohol is added to the trimethyl orthoacetate according to the process of the invention will vary depending on the scale on which the reaction is carried out. However, as a guide, it has been found that for the reaction between prenol and trimethyl orthoacetate on a 0.25 mole scale (based on the amount of prenol used), the use of an addition time of less than 30 minutes results in a reduction in the yield of methyl 3,3-dimethylpent-4-enoate. Therefore, in the process of the present invention it is preferred that the allyl alcohol is added to trimethyl orthoacetate over a period of at least 30 minutes.

It will be evident to those skilled in the art that methanol is formed as a by-product of the reaction. It follows that as the reaction presumably involves an initial interchange between the trimethyl orthoacetate and the allyl alcohol to give a mixed orthoester and methanol, it is desirable to remove methanol from the reaction mixture as it is formed in order to promote production of the mixed orthoester. Thus in the process of the present invention it is preferred to equip the reaction vessel with a means to remove the relatively low boiling methanol (bp 64.5° C.) as it is formed. This may be conveniently achieved by equipping the reaction vessel with a suitable still-head and continuously distilling the methanol from the reaction mixture during the addition of the allyl alcohol.

After the completion of the addition of the allyl alcohol to the trimethyl orthoacetate, in the process of the invention portion of the excess trimethyl orthoacetate is distilled from the reaction mixture until the reaction mixture reaches a temperature of 130° to 160° C., preferably 135° to 145° C. During this time further methanol co-distils from the reaction mixture with the trimethyl orthoacetate.

When the reaction mixture has reached a temperature of 130° to 160° C. the reaction mixture is maintained at this temperature until the reaction is complete. The time required for the completion of the reaction will vary depending on the scale on which the reaction is carried out. The completion of the reaction may be conveniently monitored by gas liquid chromatography. In practice it has been found that it is preferable to heat the reaction mixture for a period of at least 1 hour in order to complete the reaction.

On completion of the reaction following the process of the present invention the remaining trimethyl orthoacetate may be removed from the reaction mixture either by distillation or by hydrolysis with water and removal of the hydrolysis products in the aqueous phase. The γ-unsaturated carboxylic acid methyl ester may then be purified by distillation if required.

The following Comparative Examples illustrate the yields of γ-unsaturated carboxylic acid methyl esters which may be obtained by processes outside the scope of this invention.

COMPARATIVE EXAMPLE 1

A mixture of trimethyl orthoacetate (120 g; 1 mole), 3-methylbut-2-enol (21.5 g; 0.25 mole) and phenol (1.4 g; 0.015 mole) was placed in a flask equipped with a stirrer and a 10 cm fractionating column packed with Fenske rings. The mixture was heated, with stirring, to a temperature of 95°–110° C. and maintained at this temperature for a period of 2 hours while the methanol formed was collected by distillation. The excess trimethyl orthoacetate was distilled from the reaction mixture over a period of 1 hour during which time the temperature of the reaction mixture was raised to 140°–145° C. The mixture was heated, with stirring, at a temperature of 140°–145° C. for a period of 20 hours and then the product was distilled to give methyl 3,3-dimethylpent-4-enoate (14.2 g; 40%), bp 95°–99° C. at 140 mm Hg.

COMPARATIVE EXAMPLE 2

A mixture of trimethyl orthoacetate (120 g; 1 mole), 3-methylbut-2-enol (21.5 g; 0.25 mole) and orthophosphoric acid (1.5 g; 0.015 mole) was placed in a flask equipped with a stirrer and a 10 cm fractionating column packed with Fenske rings. The mixture was heated, with stirring, to a temperature of 95° to 110° C. and maintained at this temperature for a period of 2 hours while the methanol formed was collected by distillation. The excess trimethyl orthoacetate was distilled from the reaction mixture over a period of 1 hour during which time the temperature of the reaction mixture was raised to 140°–145° C. The reaction mixture was heated with stirring, at a temperature of 140°–145° C. for a period of 1 hour and then product was distilled to give methyl 3,3-dimethylpent-4-enoate (14.4 g; 40.6%); bp 95°–99° C. at 140 mm Hg.

COMPARATIVE EXAMPLE 3

A mixture of trimethyl orthoacetate (120 g; 1 mole) and orthophosphoric acid (1.5 g; 0.015 mole) was placed in a flask equipped with a stirrer and a 10 cm fractionating column packed with Fenske rings and the mixture was heated, with stirring, to a temperature of 110° C. 3-Methylbut-2-enol (21.5 g; 0.25 mole) was added to the hot reaction mixture over a period of 4 minutes and the methanol formed was collected by distillation over a period of 30 minutes. The excess trimethyl orthoacetate was then distilled from the reaction mixture over a period of 90 minutes. The product was then distilled to give methyl 3,3-dimethylpent-4-enoate (22.4 g; 63.2%), bp 70° C. at 60 mm Hg.

The invention is now illustrated by but in no way limited to, the following Examples.

EXAMPLE 1

A mixture of trimethyl orthoacetate (120 g; 1 mole) and orthophosphoric acid (1.5 g; 0.015 mole) was placed in a flask equipped with a stirrer and a vacuum-jacketed fractionating column and the mixture was heated, with stirring to a temperature of 110° C. 3-Methylbut-2-enol (21.5 g; 0.25 mole) was added dropwise to the hot reaction mixture over a period of 1 hour during which time the methanol formed was collected by distillation. On completion of the addition the reaction mixture was heated at a temperature of 110° C. for a further period of 1 hour with collection of methanol by distillation. Portion (72 g; 0.6 mole) of the excess trimethyl orthoacetate was then distilled from the reaction mixture, the distillation being continued until the reaction mixture reached a temperature of 140°–145° C. The reaction mixture was then heated to a temperature of 140°–145° C. for a period of 1.5 hours, the remaining excess trimethyl orthoacetate being allowed to condense and return to the reaction mixture. The product was then distilled to separate the remaining excess trimethyl orthoacetate and to give methyl 3,3-dimethylpent-4-enoate (29.4 g; 82.8%), bp 70° C. at 60 mm Hg.

EXAMPLE 2

A mixture of trimethylorthoacetate (62 kg) and 90% orthophosphoric acid (0.6 kg) were charged into a 90 l glass-lined mild steel reaction vessel equipped with a fractionating column and a reflux dividing head. The mixture was heated to a temperature of 102° to 105° C. and methanol and methyl acetate were distilled from the mixture as they formed. 3-Methylbut-2-enol (11 kg) was then added slowly to the reaction mixture over a period of 2 hours during which time the methanol formed was removed by distillation. When the distillation of methanol became very slow the reaction mixture was slowly heated and trimethyl orthoacetate was allowed to distil. When the reaction mixture reached a temperature close to 140° C. the reflux dividing head was switched to total reflux and the reaction mixture was heated under reflux at 135° to 140° C. until the reaction was complete (about 5 hours; reaction progress monitored by gas-liquid chromatography). On completion of the reaction the remaining excess trimethyl orthoacetate was removed by distillation.

The procedure above was repeated twice and the three product batches were combined and distilled under reduced pressure to give methyl 3,3-dimethylpent-4-enoate (43 kg; 76.5%). The combined amount of trimethyl orthoacetate recovered from the reaction was 127 kg therefore 59 kg was used in the reaction representing a trimethyl orthoacetate to 3-methylbut-2-enol ratio of 1.28:1.0.

I claim:

1. A process for the preparation of a γ-unsaturated carboxylate of formula I

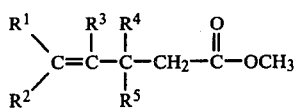

wherein $R^1$, $R^2$, $R^3$, $R^4$ and $R^5$ are independently chosen from hydrogen and $C_1$ to $C_6$ alkyl, by the reaction of an allyl alcohol of formula II

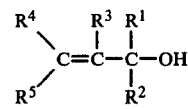

with trimethyl orthoacetate in the presence of an acidic catalyst which process comprises:
 (a) slowly adding the allyl alcohol of formula II over a period of at least 30 minutes to a stoichiometric excess of trimethyl orthoacetate heated to a temperature at or near its boiling point;
 (b) distilling portion of the excess trimethyl orthoacetate from the reaction mixture until the reaction mixture reaches a temperature in the range from 130° to 160° C.; and
 (c) maintaining the temperature of the reaction mixture in the range from 130° to 160° C. to complete the reaction.

2. A process according to claim 1 wherein in step (a) the trimethyl orthoacetate is heated to a temperature in the range of from 100°–110° C.

3. A process according to claim 1 or claim 2 wherein the temperature in steps (b) and (c) is in the range from 135° to 145° C.

4. A process according to claim 1 wherein the mole ratio of the trimethyl orthoacetate to the allyl alcohol of formula II is greater than 3:1.

5. A process according to claim 1 for the preparation of a compound of formula I wherein $R^1$, $R^2$ and $R^3$ are hydrogen and $R^4$ and $R^5$ are each methyl.

6. A process according to claim 1 wherein the acidic catalyst is an inorganic acid, Lewis acid, phenol, naphthol, aliphatic carboxylic acid, aromatic carboxylic acid, aliphatic sulfonic acid or aromatic sulfonic acid.

7. A process according to claim 1 wherein the catalyst is chosen from the group consisting of phosphoric acid, hydrochloric, sulfuric acid, aluminium chloride, zinc chloride, ferric chloride, phenol, cresol, xylenol, nitrophenol, α-naphthol, β-naphthol, the $C_1$ to $C_6$ aliphatic carboxylic acids, cyclohexane carboxylic acid, benzoic acid, the $C_1$ to $C_6$ aliphatic sulfonic acids and benzene sulfonic acid.

8. A process according to claim 1 wherein the catalyst is chosen from orthophosphoric acid and phenol.

9. A process according to claim 1 wherein the amount of catalyst employed ranges from 1 to 10 mole percent of the allyl alcohol of formula II.

* * * * *